United States Patent [19]
Tutor et al.

[11] Patent Number: 6,129,175
[45] Date of Patent: Oct. 10, 2000

[54] ACOUSTICAL CONTROL PLASTISOL EARPIECES

[75] Inventors: Michael S. Tutor; Robert W. Green, both of Memphis, Tenn.

[73] Assignee: Radians, Inc., Memphis, Tenn.

[21] Appl. No.: 09/307,524

[22] Filed: May 7, 1999

[51] Int. Cl.[7] .................................................. A61B 7/02
[52] U.S. Cl. ..................... 181/135; 181/134; 181/130; 181/129; 128/864; 128/865; 128/866; 128/867
[58] Field of Search ................................. 181/135, 134, 181/130, 129, 133; 128/864, 865, 866, 867

[56] References Cited

U.S. PATENT DOCUMENTS

| | | | |
|---|---|---|---|
| Re. 29,487 | 12/1977 | Gardner, Jr. | 128/152 |
| 3,881,570 | 5/1975 | Lewis | 181/135 |
| 4,094,315 | 6/1978 | Leight | 128/152 |
| 4,384,575 | 5/1983 | Asker | 128/152 |
| 4,461,290 | 7/1984 | Gardner, Jr. et al. | 128/152 |
| 4,465,159 | 8/1984 | Stallings | 181/129 |
| 4,490,857 | 1/1985 | Leight et al. | 2/209 |
| 4,498,469 | 2/1985 | Csiki | 128/152 |
| 4,671,265 | 6/1987 | Andersson | 128/152 |
| 4,774,938 | 10/1988 | Leight | 128/864 |
| 4,819,624 | 4/1989 | Leight et al. | 128/866 |
| 4,867,149 | 9/1989 | Falco | 128/864 |
| 5,044,463 | 9/1991 | Carr | 181/135 |
| 5,074,375 | 12/1991 | Grozil | 181/135 |
| 5,188,123 | 2/1993 | Gardner, Jr. | 128/864 |
| 5,203,352 | 4/1993 | Gardner, Jr. | 128/864 |
| 5,319,163 | 6/1994 | Scott | 181/130 |
| 5,333,622 | 8/1994 | Casali et al. | 128/864 |
| 5,727,566 | 3/1998 | Leight | 128/857 |
| 5,741,824 | 4/1998 | Butschbacher et al. | 521/73 |
| 5,756,555 | 5/1998 | Wesch et al. | 9/30 |
| 5,781,272 | 7/1998 | Bright et al. | 351/123 |
| 5,792,998 | 8/1998 | Gardner, Jr. et al. | 181/130 |
| 5,904,143 | 5/1999 | Magidson et al. | 128/864 |

OTHER PUBLICATIONS

*Handbook of Polyvinyl Chloride Formulating*, § 2.3.4, pp. 35–37; §§ 5.4.5–5.4.9, pp. 207–221; §§ 20.8–20.18, pp. 534–547 (Edward J. Wickson ed., John Wiley & Sons 1993).
*Plastisols and Organosols*, pp. 8–23; pp. 33–59 (Harold A. Sarvetnick ed., Van Nostrand Reinhold Co. 1972).

*Primary Examiner*—David Martin
*Assistant Examiner*—Edgardo San Martin
*Attorney, Agent, or Firm*—Walker, McKenzie & Walker, PC

[57] ABSTRACT

An acoustical control earpiece comprised of non-foamed polyvinyl chloride plastisol. The earpieces may be acoustical hearing protective earplugs as well as overmolds and covers for audio sound reproduction devices such as headphones, speakers, and hearing aids, and may be used alone or in conjunction with hearing protector bands or eyewear. The earplugs may have an open or closed internal void therewithin, are adapted for receipt into the concha and ear canal of a wearer. The earpieces may be formed by injection molding, roto-molding, or slush molding. The hardness of the earpieces has a 00 Durometer hardness value of about 10 to 90 and preferably ranging 40 to 60.

20 Claims, 6 Drawing Sheets

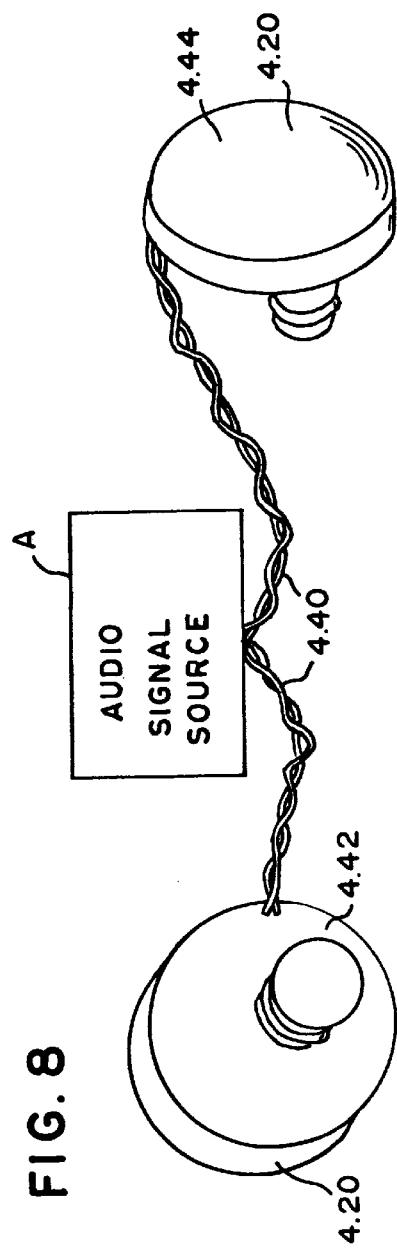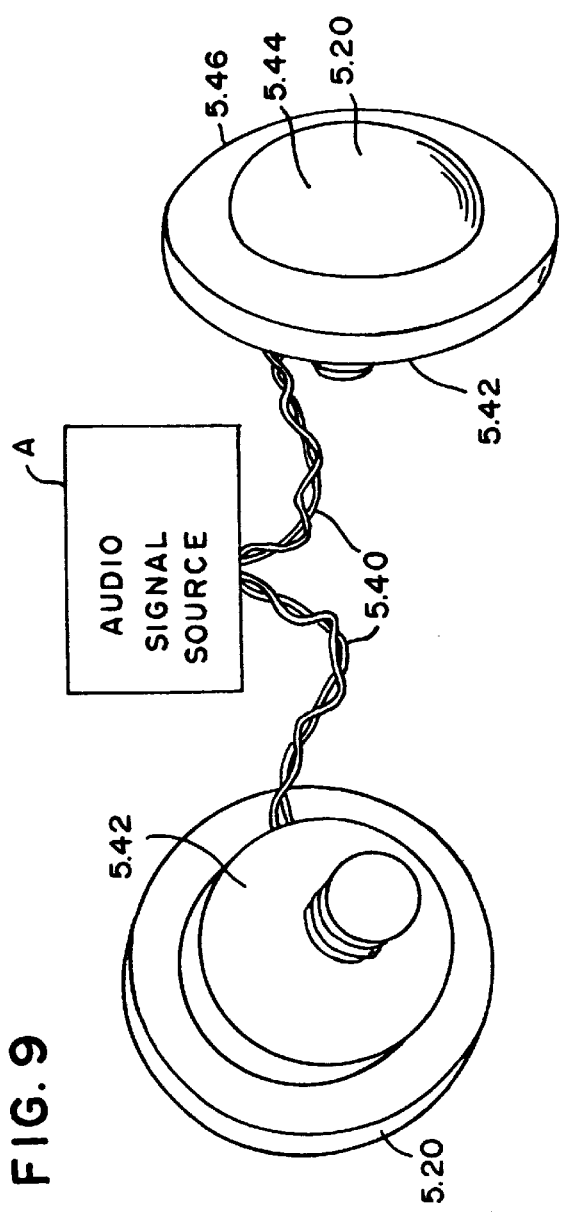

ACOUSTICAL CONTROL PLASTISOL EARPIECES

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates, in general, to safety devices, and in particular, to earplugs and earpieces that protect the hearing of a human being.

2. Description of the Prior Art

Plastisol is a composition well-known to those skilled in the art, and "plastisol", as that term is used herein and as known by those skilled in the art, can be defined as follows:

Plastisols . . . in their simplest form, are dispersions of fine-particle-size PVC resins in liquid vehicles consisting of plasticizers, plasticizers plus dilutents, or plasticizers plus solvent and stabilizers. Typical ingredients of commercial plastisols include dispersion resins, blending resins, plasticizers, stabilizers, fillers, pigments, thinners, blowing agents, viscosity modifiers, flame retardants, smoke suppressants, adhesion promoters, release agents, and specialty additives such as UV screeners, air release promoters, and moisture absorbers.

*Handbook of Polyvinyl Chloride Formulating*, § 2.3.4 at p. 35 (Edward J. Wickson ed., John Wiley & Sons 1993).

It should be noted that this broad definition of plastisol encompasses both "foamed" and "non-foamed" (or "unfoamed") variants of plastisol.

Well-known prior art texts also describe polyvinyl chloride ("PVC") plastisol and its various forms, with one such description being as follows:

Plastisols are a unique liquid form of "vinyl" compound in the unprocessed state. A plastisol is a suspension of PVC in a liquid plasticizer to produce a fluid mixture which may range in viscosity from a pourable liquid to a heavy paste. This fluid may be spread onto a substrate, poured into a mold, sprayed onto a surface, etc. The plastisol is converted into a homogeneous "vinyl" product through exposure to heat, e.g., 350 degrees F, depending on the specific ingredients used. The heat causes the suspended resin to be "Fused" or dissolved in the plasticizer. Upon cooling, a flexible vinyl product (depending on the recipe used) is formed, with little or no shrinkage. The addition of solvent to a plastisol for reduction of viscosity is common practice, particularly for coatings applications. This mixture is referred to as an organosol.

The resin ingredient is polyvinyl chloride, or a vinyl chloride copolymer, e.g., a vinyl chloride—vinyl acetate copolymer. Unplasticised polyvinyl chloride is a rigid polymer. A variety of plasticizers may be used. The type and amount will affect (modify) the plastisol viscosity and processing characteristics as well as the flexibility and properties of the finished article. Flexibility normally ranges from semirigid to soft and pliable, although, through modification with other polymers as well as through special processing techniques, the range of properties may be extended to include rigid forms. At high plasticizer levels plastisols exhibit high elongation, softness, desirable "hand" or "feel" and good abrasion resistance. Typical examples are doll parts and vinyl upholstery. As plasticizer content is reduced, flexibility and elongation decrease, and hardness, tensile strength and abrasion resistance increase. Typical examples are floor coverings and tool handles.

Adapted from *Plastisols and Organosols*, (Harold A. Sarvetnick ed., Van Nostrand Reinhold Co. 1972).

There are several broad groups or forms of materials made from plastisol, namely, plastics, foams, coatings, and adhesives.

The well-known plastic form of plastisol includes a variety of products that may be cast (injection molded), rotational molded ("roto-molded"), slush molded, or dip molded. Examples of such plastic plastisol products include toys, printing plates, floor mats, fishing lures, inflatable balls, traffic cones, automobile arm rests, waterproof boots for the foot, etc.

The well-known foam form of plastisol ("foamed plastisol") can be used to make products such as athletic padding, mats, life preservers, boat bumpers, automobile gaskets, automobile body insulation, inner soles for use in footwear, etc.

The well-known coating form of plastisol is used for coating upholstery, clothing, gloves, shoes, tents, and film as well as for floor coverings and carpet backing.

A broad range of adhesives are made from plastisol. Such adhesives are used as automobile undercoatings, seam sealers, and for bonding vinyl to fabric.

Additionally, various types of earplugs, earpieces, and ear cushions for earphones and other audio devices, such as hearing aids, are well known. Some of the better prior art earplugs on the market are made from foamed plastisol, such as the earplugs described in Gardner, Jr., U.S. Pat. No. Re. 29,478 (reissued Dec. 6, 1977). However, these prior art earplugs are inferior in that comfort is compromised in exchange for effective sound attenuation or vice-versa. The result of this compromise is either that the earplugs have inferior sound attenuation quality or else are uncomfortable, in which case the user wears them incorrectly or avoids wearing them completely, thereby defeating the sound attenuation and safety purpose of using the earplugs.

Prior art earplugs are also unhygienic. A problem associated with many prior art earplugs is the requirement that they be "rolled down" or compressed to a smaller diameter by the earplug user before insertion into his or her ear canal. This compression of prior art earplugs is necessary so that a sealingly tight fit can be obtained between the earplug and the user's ear canal as the earplug subsequently expands, thereby sealingly protecting the user's ear, by sound attenuation, from injury that would otherwise occur due to excessively loud sound noise. Because the workplace can be an unsanitary environment, the repeated use of roll-down earplugs inherently gives rise to opportunities for unsanitary conditions in which any contamination on an earplug user's hands is then transferred to the user's ears as the earplugs are compressingly "rolled down" and then inserted into the his or her ears. Prior art foamed plastisol earplugs, such as those described, for example, in Gardner, Jr., U.S. Pat. No. Re. 29,478 (reissued Dec. 6, 1977), are also susceptible to absorbing liquids and to picking up foreign matter because they are sponge-like in nature. This can lead to adverse health situations caused by irritation or sensitizing of the thin layer of skin that forms the wall of the ear canal. Prior art earplugs made of latex are less than desirable because a portion of the population is allergic to latex. Other materials used in making prior art earplugs tends to be relatively harder than prior art latex or foamed plastisol earplugs, thereby causing the ear canal to become irritated with repeated insertion and extraction of the earplugs.

Many prior art earpieces subject the user's concha and ear canal to a slightly tacky or abrasive surface that, in the case of foam earpieces, is also absorbent. The epidermal permeability barrier in the ear and ear canal is easily compromised by repeated insertion and extraction of a tacky or abrasive object which, by the nature of its surface, tends to wear away the stratum corneum. Earpieces having curved flanges or skirts are also less than desirable because they are constructed in a way that allows the sharp edge of the flange or skirt to scrape against the concha and ear canal walls when extracted. Foam earpieces are doubly-damaging to the epidermal permeability barrier because their absorbent properties may tend to encourage transepidermal water loss from the basal or germinative layer of the epidermis, thereby causing dry skin in the ear canal and concha immediately adjacent to the ear canal. Degradation of the epidermal permeability barrier can result in discomfort and, in some cases, inflammation of the concha or ear canal.

It is therefore desirable to have an improved earplug or earpiece that is hygienic and that is sufficiently comfortable to be worn for extended periods without discomfort.

BRIEF SUMMARY OF THE INVENTION

The present invention is an acoustical control earplug or earpiece, comprised of non-foamed polyvinyl chloride plastisol of the plastic form, that is sized and adapted for receipt into a human being's concha and/or ear canal. The present invention eliminates the problems of prior art foamed plastisol earplugs by using non-foamed plastisol to create a supple earpiece that has both effective sound attenuation and superior comfort. If the wearer is comfortable, then effective placement and use of the hearing protection earpiece becomes substantially less problematic. It has been found that non-foamed polyvinyl chloride plastisol has excellent acoustical sealing properties against human skin within a human ear while, at the same time, providing superior comfort as compared with prior art devices.

The earplug or earpiece may have a closed or open internal void formed therewithin to allow for compression of the device as it is inserted into a wearer's ear canal. The device may also be used as a covering for an electrical to audio sound reproduction device such as an earphone or hearing aid so as to provide comfort for wearing the sound reproduction device while simultaneously sealingly attenuating outside noise from reaching the ear canal.

It is an object of the present invention to provide an earplug/earpiece having effective sound attenuation and superior comfort. It is a further object of the present invention to provide a reusable earplug/earpiece that is also substantially more hygienic than prior art devices. Because the present invention, unlike prior art foamed earplugs, does not need to be "rolled down" prior to insertion into the ear canal, and because the present invention can easily and non-destructively be washed in soap and water prior to reuse, the present invention is substantially more hygienic than prior art devices. The non-foamed polyvinyl chloride plastisol used for the present invention is available in U.S. Food and Drug Administration ("FDA")-approved formulations.

The present invention may be molded using injection molding, slush-molding, roto-molding, or other casting techniques, and may be formulated with a range of firmness to optimize use in different environments. The earpiece/earplug may include small metallic tracers to facilitate magnetic detection of the earpiece/earplug. Shapes and sizes may vary to accommodate stand-alone use or use in combination with headbands, eyewear, or audio listening devices.

BRIEF DESCRIPTION OF THE SEVERAL VIEWS OF THE DRAWING

FIG. 8 shows perspective views of a fourth embodiment of the present invention as a cover or overmold for a smaller audio listening device.

FIG. 9 shows perspective views of a fifth embodiment of the present invention as a cover or overmold for a larger audio listening device.

DETAILED DESCRIPTION OF THE INVENTION

Figure 2:
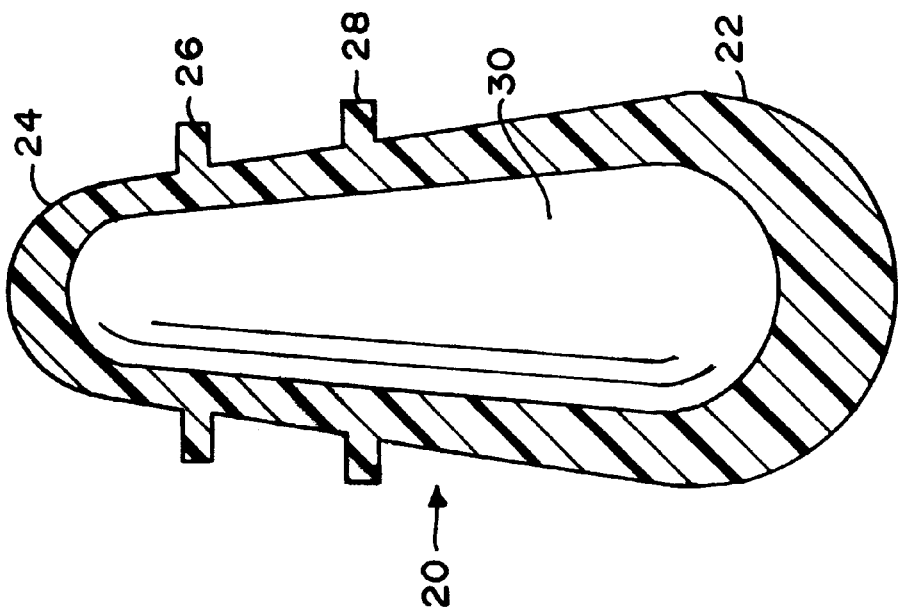
FIG. 2 is a longitudinal cross-sectional view of the first embodiment of the present invention taken along the axis of the first embodiment. All longitudinal cross-sectional views along the axis of the first embodiment are substantially the same.

Referring to FIGS. 1–9 and 13–14, the present invention is seen to include various embodiments of an earpiece made from non-foamed polyvinyl chloride ("PVC") plastisol, with the plastisol being the plastic form of plastisol. It should be understood, however, that the term "earpiece", as used herein, is defined and shall be broadly construed to encompass not only the earplugs of the first embodiment (FIGS. 1–2), second embodiment (FIGS. 3–5), third embodiment (FIGS. 6–7), and sixth embodiment (FIGS. 13–14) of the present invention, but also the covers/overmolds for earphones, headphones, or hearing aids and the like of the fourth embodiment (FIG. 8) and fifth embodiment (FIG. 9) of the present invention.

The present invention is a specific application of a range of chemical formulations. These formulations produce a relatively soft earpiece that falls within one of the generally accepted categories of plastisol, namely, the plastic form of plastisol.

The various embodiments of the plastisol earpiece of the present invention are made of "non-foamed" polyvinyl chloride ("PVC") plastisol, as distinguished from prior art "foamed" polyvinyl chloride plastisol earpieces. The well-known term "foamable" or "foamed", as known and used in the art in connection with plastisols, indicates the presence of a blowing agent or microbeads within the plastisol, and is defined to be "any flexible polymeric material which can be foamed" as given, for example, in Gardner, Jr., U.S. Pat. No. Re. 29,487 (reissued Dec. 6, 1977), hereby fully incorporated by reference herein, so as to result in an ultimately foamed earplug structure meeting a given recovery rate and pressure criteria. In contrast, "non-foamed" or unfoamed plastisol, as that term is defined and as used in the present invention, lacks a blowing agent or embedded encapsulated microspheres or microbeads and therefore lacks a foamed structure.

Prior art has addressed the need for earplugs to be either compressible, deformable, or both. The present invention takes advantage of the supple qualities of non-foamed polyvinyl chloride plastisol to seal against the skin within the human ear to create a sound attenuation environment for the ear using both the compressible and deformable characteristics of non-foamed polyvinyl chloride plastisol to optimize sound control and comfort.

Earplugs and earpieces are of three general forms. So-called "aural" earplugs and earpieces insert into the ear canal of the wearer and substantially block the ear canal. So-called "semi-aural" earplugs and earpieces are partially inserted into the ear canal and also block the entrance of the ear canal in the concha. So-called "supra-aural" earplugs and earpieces block the entrance to the ear canal in the concha without entering the ear canal itself. It shall be understood that the terms "earplugs" and "earpieces", as used herein, have a scope that encompasses all three of the aural, semi-aural, and supra-aural forms.

The present invention provides an earpiece that has a lubricious nonabsorbent, non-tacky and non-abrasive surface that is innocuous to the human skin. The supple nature of the plastisol, formulated and molded as presented herein, conforms to each wearer's unique ear canal structure for a precise, comfortable, and occlusive seal. The plastisol of the present invention has been found to have unique pressure-reducing characteristics that minimize lateral pressure on the ear canal walls, thereby lessening the likelihood of wearer tension and fatigue.

From a dermatological vantage point, the present invention provides a significant improvement in protecting the epidermal permeability barrier of the skin in the concha and ear canal. Plastisol, as formulated for the present invention, uses FDA-approved materials that are acceptable for prolonged contact with human skin. The lubricious and supple surface of the present invention minimizes the adverse affects of constant insertion and extraction of the earpieces, thereby preserving the stratum corneum that forms a structural and adaptive barrier to the environment and plays an important physiological role. Although the stratum corneum is only a thin biological membrane, it plays a key role in maintaining human life in the atmosphere because its efficient barrier function inhibits loss of water from human water-saturated living tissues, thereby preventing desiccation of the body. This barrier function is important for sustaining life because it prevents invasion of damaging substances including microorganisms.

In addition to their supple nature, the non-foamed acoustically-active plastisol earpiece of the present invention has been found to have excellent sound attenuation characteristics. The term "acoustically active", when used in connection with the non-foamed plastisol of the present invention, refers to the acoustic vibration dampening and substantial sound transmission loss properties of the non-foamed plastisol of the present invention. The mastoid process of the human ear is known to be particularly sensitive to physical vibrations being transmitted by articles touching the head, such as glasses, headbands, protective hard hats without an isolation web, etc. If a person is in a close working environment where his or her hearing protector band or safety glasses comes in proximity with machinery or other sources of mechanical vibration, the mastoid will pick up the vibration transmitted via the hearing protector band or safety glasses. The suppleness of the non-foamed PVC plastisol composition, and the shape of the earpieces of the present invention constructed of that composition, provide sound attenuation of mechanical and acoustical vibration by acoustic isolation of the tympanic membrane of the wearer's ear and by vibrational isolation of the mastoid process and bony structure surrounding the ear.

The present invention provides improved comfort and hygienic superiority over prior art foamed plastisol earplugs. The non-foamed PVC plastisol composition of the present invention has been found to resist absorption of foreign materials and to be washable without deterioration. The earpieces of the present invention work well in dusty and wet environments. Testing of the earpieces of the present invention has shown that they can be worn for extended periods of time without discomfort and that they provide excellent hearing protection, as shown by testing results discussed hereinafter.

Plastisol compositions used in the present invention are composed of dispersion-type polyvinyl chloride homopolymers or copolymers dispersed in various plasticizers, primarily in the phthalate, adipic or tremellitate families, sometimes with so-called hydrocarbon secondaries to reduce cost and specific gravity. Mixed metal heat stabilizers and auxiliary stabilizers may be added to the formulation to reduce the release of hydrogen chloride during processing and to reduce degrading of the polymer. Other additives, such as fillers and pigments, may be added to change physical properties or add color. The preferred compositions are stable in storage and show good gelation properties. Some plasticizers have better air release properties than others, and the preferred plasticizers used in formulations 1 through 4 of the present invention discussed hereinbelow were chosen to have good to excellent air release properties. Additionally, small amounts of surface active agents ("surficants") and metallic soaps can be added to the plastisol formulation, in a manner well-known to those skilled in the art, to enhance air release from the plastisol during processing, heating and curing. The choice of plasticizers having good to excellent air release properties is preferred to prevent air bubbles, not only to ensure that devices of the present invention are hygienic and will not absorb or collect foreign matter within cavities on the surface of the earpieces, but also to ensure that the devices of the present invention have a substantially uniform consistency and a controlled, constant resilience. As further detailed below, devices based on such formulations of plastisol have been determined to have good comfort and noise-damping properties. The presence of occasional air bubbles, although considered undesirable in the present invention, will not, except in extreme cases, cause the earpieces of the present invention to be unusable, but would might cause a loss in cosmetic quality and appeal of the earpieces. It should be reiterated that the formulation and manufacture of the present invention is specifically intended to remove air bubbles, and the plastisol formulation of the present invention does not produce a "foamed" product, but instead produces the plastic form of plastisol.

The present invention is preferably molded from an emulsion-type plastisol material. There are a range of formulations that will produce satisfactory results. When formulating the plastisol, about 65 to 90 percent of the compound will consist of monomeric plasticizers to include, but not limited to adipates, phthalates, and trimellitates. Preferably, the monomeric plasticizer consists of about 67.8 percent dioctyl adipate and 11.9 percent dioctyl phthalate. Polymeric plasticizers which may be used include, but are not limited to: the dibasic acid group such as sebacic acid, azelaic acid, adipic acid, glutaric acid; the gylcols such as 1,2 propylene, 1,3 butylene, 1,4 butylene, and neopentyl; terminating agents such as monobasic fatty acids, alcohol, hydroxyl, and post termination treatments such as acetylation.

There are certain useful epoxy plasticizers including, but not limited to; vegetable oils such as soybean oil, linseed oil and others representing naturally-occurring triglycerides, e.g., tris esters of glycerol and mixed unsaturated fatty acids; alkyl esters of oleic acid, and alkyl esters of tall oil fatty acids, e.g., epoxytallates or epoxytofates; epoxides of tall oil fatty acid bis-esters of ethylene and propylene glycol, e.g., bis-epoxides. Preferably the compound includes 1.7 percent epoxyized soybean oil.

Resins including polyvinyl homopolymers and copolymers preferably used in plastisol formulating the present invention may include, but are not limited to, vinyl chloride, vinyl acetate, vinylidene chloride, ethylene, and propylene. The compound may consist of about 10 to 30 percent vinyl chloride and selective use of copolymers such as vinyl acetate, vinylidene chloride, maleic ester, and acrylonitrile. Preferably the compound includes about 16.9 percent vinyl chloride resin with an average particle size suitable for dispersion-type plastisols.

Stabilizers may be added to enhance the overall formulation such as zinc, usually phosphites, e.g., tris (nonylphenl) phosphite with very minor quantities of zinc salts, zinc powder mixed with polyol as synergist, and/or phosphites with minor amounts of calcium and zinc. Other stabilizer combinations can be achieved using barium, cadmium and zinc in various combinations. Some phosphite liquids are relevant as well as combinations of tin, cadmium and zinc. Preferably, the compound includes about 1.7 percent calcium-zinc heat stabilizer.

Fire retardants may be added to the formulation as appropriate. Generally, the use of antimony compounds and extended products is indicated. However, metal hydroxides, hydroxycarbonates, and carbonates, as well as molybdenum, zinc and iron compounds, may also be used. Additionally, chlorinated paraffin should preferably be included as a flame suppressant. Preferably, the compound may include about 0.8 percent antimony trioxide and about 7 percent chlorinated paraffin.

Magnetic metal particles may be included in the formulation to allow for magnetic detection of earplugs lost in manufacturing, food processing, or other situations where the presence of foreign material is adverse. Pigments are preferably added to produce a desired color or colors including metallic colors.

Such vinyl chloride based polymers are suitable for compounding into a plastisol for molding, dipping, or casting. The family of compounds addressed here represents the cross section of components from which suitable plastisols may be molded, dipped, or cast into suitable hearing attenuation devices or covers for audio devices. However, these compounds are only representative and are not intended to exclude other products that could also produce a plastisol compound suitable for molded, dipped, or cast earpieces.

Injection molding, roto-molding, slush molding, mold casting, or dipping may be used for producing the earpieces of the present invention.

Roto-molding is a process where the mold is partially filled with plastisol material, then closed. The mold is constantly rotated in two axes while the plastisol cures to a uniform thickness on the mold's interior surface, thereby leaving a void in the center of the molded plastisol.

Slush-molding is a process where one end of the mold is open. The plastisol is poured into the open end of the mold, and the mold is then cooled from the outside in using cold water. Satisfactory gelation properties are very important in slush molding.

Plasticizers and plasticizer mixtures are poor solvent for solid PVC resins at room temperature; but as the temperature of a plastisol is raised, the plasticizer first penetrates, then swells and solvates the resin. During this process the plastisol changes from a liquid into a gelatinous solid. Then at higher temperatures the plasticizer or plasticizer mixture helps the resin to fuse, with the development of physical properties after cooling similar to those of a plasticizer PVC part formed by hot-melt processing. Fusion occurs when PVC molecules in adjacent PVC particles get thoroughly entangled with each other and an integral part or web develops.

*Handbook of Polyvinyl Chloride Formulating*, § 2.3.4 at p. 35 (Edward J. Wickson ed., John Wiley & Sons 1993).

Good gelation is defined as having a gelatinous, homogeneous consistency with no entrained air bubbles or unabsorbed ingredients.

The preferred method of manufacture of the earpieces of the present invention is by injection molding used with temperature controls maintaining a temperature range of 325° to 385° Fahrenheit (163° to 196° Celsius), preferably about 350° Fahrenheit (177° Celsius) for fusion of the compound. Hardness of the material is established by the amount of polymer resin included in the formulation, in a manner well-known to those skilled in the art. As the amount of polymer in the formula is increased, the hardness of the resulting earpiece increases. For optimum comfort and sound attenuation, the earpiece of the present invention is made from a formula that results in a 00 Durometer hardness value (ASTM D2240) of between about 10 and 90 (on a scale of 0 to 100), and preferably between about 40 and 60.

Upon removal from the mold, a curing process of three days is typically required before testing the earpiece for hardness.

For example, earpieces of the present invention for use in Arctic temperatures should be on the softer end of the hardness range, perhaps closer to a 00 Durometer hardness value of 10. For hotter environments, such as the industrial environment found in a foundry or experienced by a worker on the tarmac of a landing field or in a desert, earpieces on the harder end of the hardness range, perhaps closer to a 00 Durometer hardness value of 90, might be desirable. For normal usage in room temperature factory environments, the earpieces of the present invention should be formulated to have a 00 Durometer hardness value of between about 40 to 60.

As to the physical characteristics of the earpieces of the present invention, the shape and configuration of the various embodiments of the earpiece varies according to the requirements of different applications.

Figure 1:
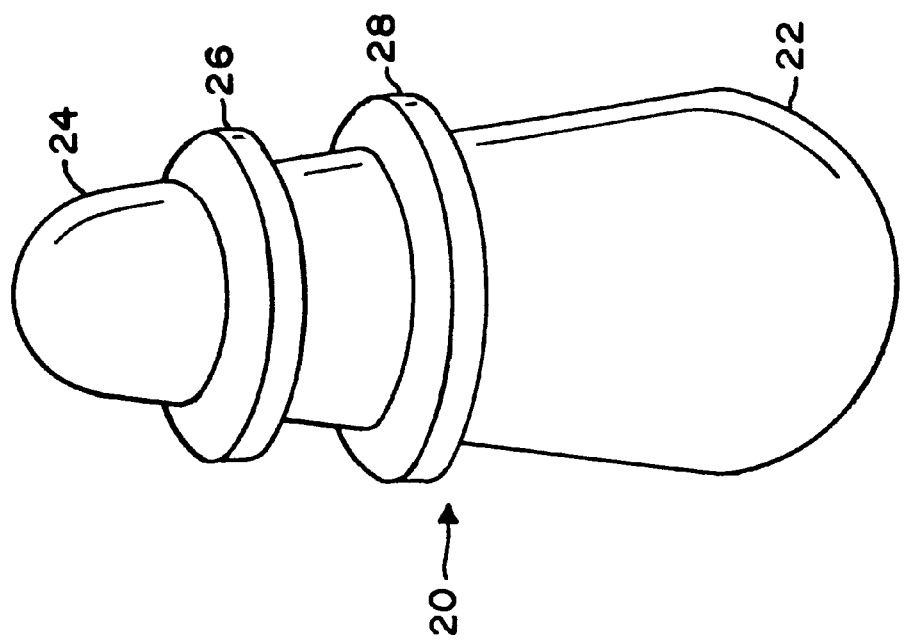
FIG. 1 is a side perspective view of a first embodiment of the present invention. The view from all sides is substantially the same.

Referring to FIGS. 1–2, a first preferred embodiment of the present invention is seen to comprise a stand-alone earplug 20, preferably cylindrically symmetrical along an axis and being bullet-shaped, with a base 22 configured to rest in the concha of the ear of the user and a nose 24 configured to enter and substantially block the auditory canal of the ear of the user. The base 22 of the earplug 20 nestles in the concha and is effectively held in place. The diameter of the earplug 20 ranges from about 3/16 inch (0.476 cm) to about 9/16 inch (1.43 cm), with the nominal diameter being smallest at the nose 24 of earplug 20 and reaching its maximum at the base 22 of the earplug 20. The length of earplug 20 preferably ranges from about ¾ inch (1.91 cm) to about 1.5 inches (3.81 cm). The nose portion 24 of earplug 20 may have one or more deformable highly flexible disks 26, 28 for the purpose of creating multiple layers of sound blocking and for enhancing comfort. The disks 26, 28 are mounted laterally on the nose 24 of the earplug 20 so as to form flexible encircling flanges as shown. Individual disks 26 may vary in diameter to facilitate acoustically isolating different size ear canals. Earplug 20 preferably has an internal void 30 formed therewithin that may be of varying dimensions to allow compression of the earplug 20. Roto-molding or slush molding, as heretofore described, may be used to form a closed internal void 30 within earplug 20. Internal void 30 allows for compression of the earplug 20 before insertion into the ear canal of the user. The preferred embodiment of the stand-alone earplug 20 measures about 3/16 inch (0.476 cm) in diameter at nose 24, 7/16 inch (1.11 cm) in diameter at base 22, and 1.125 inches (2.86 cm) in length along the axis.

Figure 5:
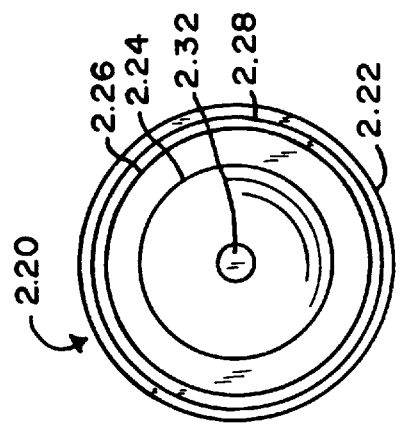
FIG. 5 is an end view of the second embodiment of the present invention, taken substantially along the line 5—5 shown in FIG. 3.
Figure 4:
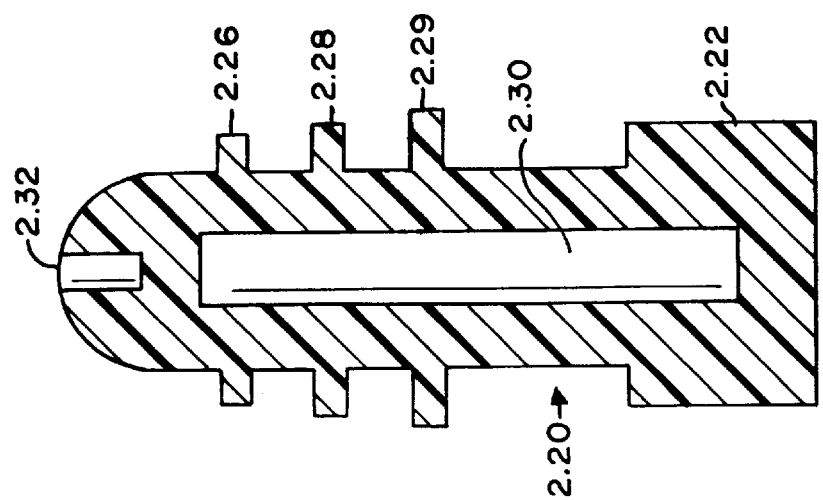
FIG. 4 is a longitudinal cross-sectional view of the second embodiment of the present invention. All longitudinal cross-sectional views along the axis of the second embodiment are substantially the same.
Figure 3:
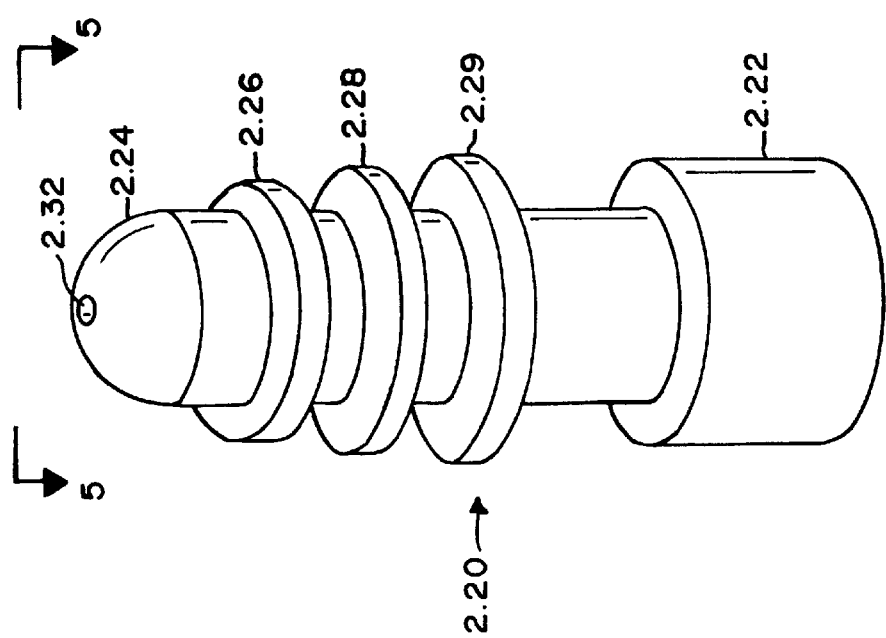
FIG. 3 is a side perspective view of a second embodiment of the present invention. The view from all sides is substantially the same.

A second preferred embodiment of the present invention is shown in FIGS. 3–5, with identifying reference designators marked similarly to the first embodiment, except with the prefix "2.". It shall be understood that many aspects of all embodiments are substantially the same, and only the differences will be treated in detail. The various compositions and formulations of non-foamed polyvinyl chloride plastisol described herein shall be understood to apply equally to all embodiments of the invention, and the only significant structural difference between the first three embodiments is their shape.

Referring to FIGS. 3–5, the second preferred embodiment of the present invention is seen to comprise a stand-alone earplug 2.20, preferably cylindrically symmetrical along an axis and being bullet-shaped, with a base 2.22 configured to rest in the concha of the ear of the user and a nose 2.24 configured to enter and block the auditory canal of the ear of the user. The base 2.22 of the earplug 2.20 nestles in the concha and is effectively held in place. The diameter of the earplug 2.20 ranges from about 3/16 inch (0.476 cm) to about 9/16 inch (1.43 cm), with the nominal diameter being smallest at the nose 2.24 of the earplug 2.20 and reaching its maximum at the base 2.22 of the earplug 2.20. The length of earplug 2.20 preferably ranges from about ¾ inch (1.91 cm) to about 1.5 inches (3.81 cm). The nose portion 2.24 of the earplug 2.20 may have one or more deformable highly flexible disks 2.26, 2.28, 2.29 for the purpose of creating multiple layers of sound blocking and enhancing comfort. The disks 2.26, 2.28, 2.29 are mounted laterally on the nose 2.24 of the earplug 2.20 so as to form flexible encircling flanges as shown. Individual disks 2.26 may vary in diameter to facilitate acoustically isolating different size ear canals. Earplug 2.20 has an internal void 2.30 formed therewithin that may be of varying dimensions to allow compression of the earplug 2.20. Earplug 2.20 also has a blind bore 2.32 formed as shown in the center of the nose portion 2.24 to further allow compression of the earplug before insertion into the ear of the user. Roto-molding, as heretofore described, may be used to form a closed internal void 2.30 within earplug 2.20. Internal void 2.30 allows for compression of the earplug 2.20 before insertion into the ear of the user. The preferred embodiment of the stand-alone earplug 2.20 measures about 3/16 inch (0.476 cm) in diameter at nose 2.24, 7/16 inch (1.11 cm) in diameter at base 2.22, and 1.125 inches (2.86 cm) in length along the axis.

Figure 7:
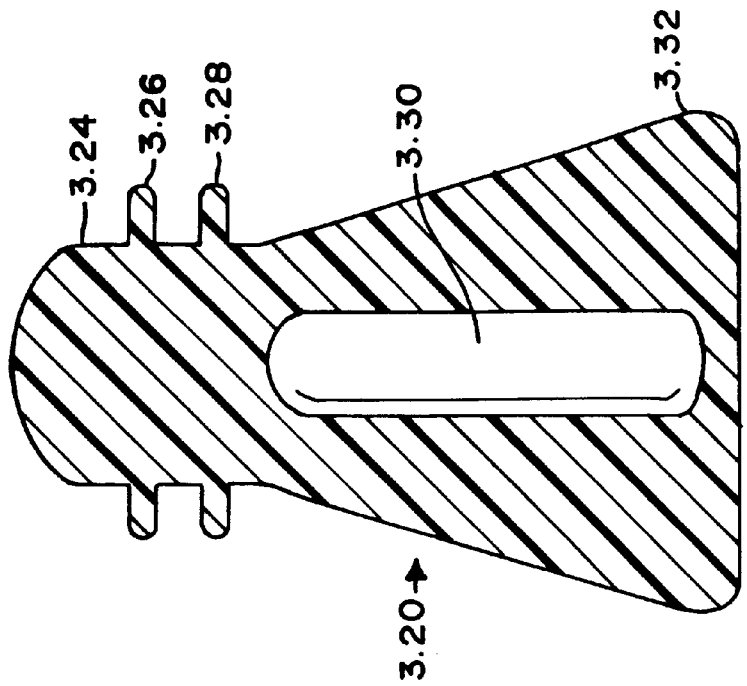
FIG. 7 is a longitudinal cross-sectional view of the third embodiment of the present invention. All longitudinal cross-sectional views along the axis of the third embodiment are substantially the same.
Figure 6:
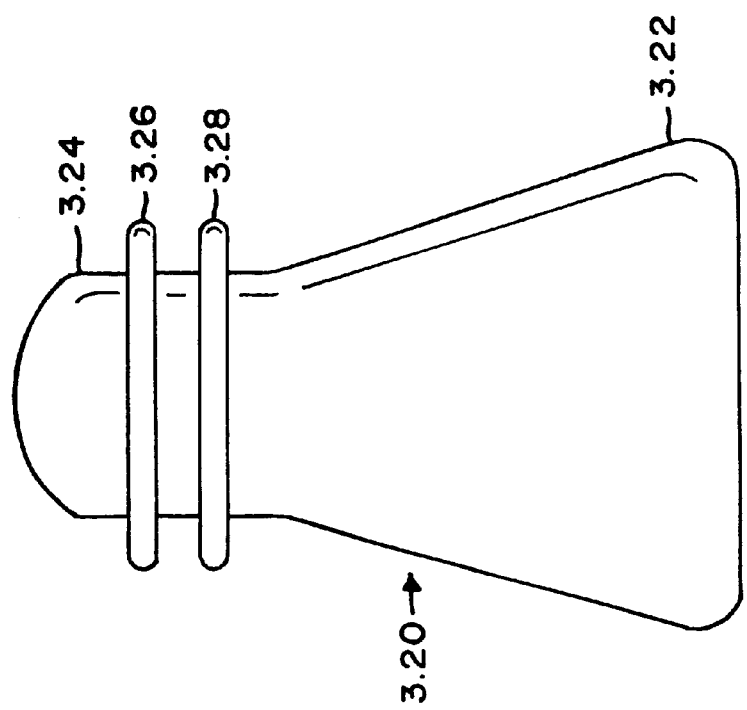
FIG. 6 is a side view of a third embodiment of the present invention. The view from all sides is substantially the same.

A third preferred embodiment is shown in FIGS. 6–7, with identifying reference designators marked similarly to the first and second embodiments, except with the prefix "3." It shall be understood that many aspects of all embodiments are substantially the same, and only the differences will be treated in detail.

Referring to FIGS. 6–7, earplug 3.20 is intended for use in conjunction with a headband or with eyewear as envisioned in Bright et al., U.S. Pat. No. 5,781,272 (issued Jul. 14, 1998), fully incorporated by reference herein. Earplug 3.20 is adapted to be fittingly received over a barb attached to a headband or the temple of eyewear. Earplugs 3.20 of this type generally measure approximately 11/16 inch (1.75 cm) to about 1.188 inches (3.02 cm) in length, having a diameter ranging from about ½ inch (1.27 cm) to about ¾ inch (1.91 cm) at the base 3.22 and from about 3/16 inch (0.476 cm) to 7/16 inch (1.11 cm) at the nose 3.24. The earplug 3.20 may be more particularly described as having a conical base 3.22 measuring about ½ inch (1.27 cm) to about ¾ inch (1.91 cm) in diameter, extending approximately about ½ inch (1.27 cm) to about ¾ inch (1.91 cm) in length, and having an outer angle of about 10 to 30 degrees as measured between the center axis to the outer surface. The conical base 3.22 of the earplug 3.22 represents about ⅔ of the length of the earplug 3.22. The remaining about ⅓ of the length of the substantially cylindrical earplug 3.22 is composed of nose 3.24, which has a diameter of about 3/16 inch (0.476 cm) to about 7/16 inch (1.11 cm) and an axial length of about 3/16 inch (0.476 cm) to about 7/16 inch (1.11 cm). The cylindrical nose portion 3.24 of the earplug 3.22 may have one or more deformable highly flexible disks 3.26, 3.28 for the purpose of creating multiple layers of sound blocking and enhancing comfort. The disks 3.26, 3.28 are mounted laterally on the nose 3.24 so as to form flexible flanges thereabout. Individual disks 3.26, 3.28 may vary in diameter to facilitate acoustically isolating different size ear canals. The earplug 3.22 may be injection molded or roto-molded to produce an earplug 3.22 either with or without a closed void 3.30 in the center. The presence of the void 3.30 allows the earplug 3.20 to be fittingly received over the end of a barb on a headband or other device and may also serve as a way to attach the earplug 3.20 to the temple of eyewear. The preferred embodiment of the earplug measures ⅞ inch (2.22 cm) long, having a base 3.20 measuring about ¹¹⁄₁₆ inch (1.75 cm), a nose 3.24 measuring about ⁵⁄₁₆ inch (0.794 cm), disks 3.26, 3.28 measuring about ¹⁄₃₂ inch (0.079 cm) and a conical angle of about 20 degrees. The earplug 3.20 will enter the ear canal between the tympanic membrane and the external auditory meatus, and the cylindrical nose 3.24 passes through the external auditory meatus and into the ear canal, thereby blocking the ear canal. The 20-degree angle allows a second blocking to occur where the ear canal departs from the external auditory canal, with the conical base 3.22 portion sitting in the concha of the ear narrowing into the ear.

A fourth preferred embodiment is shown in FIG. 8, with identifying reference designators marked similarly to the first, second, and third embodiments, except with the prefix "4.". Likewise, a fifth preferred embodiment is shown in FIG. 9, with identifying reference designators marked similarly to the other embodiments, except with the prefix "5.". It shall be understood that many aspects of all embodiments are substantially the same, and only the differences will be treated in detail.

Referring to FIGS. 8 and 9, earpieces 4.20 and 5.20 are shown as covers or boots of plastisol for a well-known audio listening device such as a headphone or hearing aid respectively supplied, over wires 4.40, 5.40, with an electrical signal representation of an audio signal from an audio signal source A. Earpiece 4.20 may also be configured for use with a band or eyewear as envisioned in Bright et al., U.S. Pat. No. 5,781,272 (issued Jul. 14, 1998). Use of a plastisol cover or boot for a earphone or hearing aid increases comfort for the wearer while avoiding the unsanitary conditions sometimes associated with repeated use of foam covers or boots. The substantial difference between earpieces 4.20 and 5.20 is that the electromagnetic sound-generating element 5.42 shown in FIG. 9 is larger than the sound-generating element 4.42 shown in FIG. 8, thereby providing greater volume and a wider range of frequency reproduction in a manner well-known to those skilled in the art. Earpieces 4.20 and 5.20 have convex portions 4.44 and 5.44, respectively, that are adapted for being received into the concha of a user's ear. Because of its larger size, earpiece 5.20 may have an enlarged outwardly-extending flange 5.46 that sealingly rests against the pinna or outer ear of the wearer. Plastisol covers or boots of earpieces 4.20, 5.20 may easily be washed or replaced for hygienic reasons or after deterioration due to extended wear. The preferred embodiments will vary in thickness depending on the configuration of the sound-generating element being covered but will have an average thickness of about ¹⁄₃₂ inches (0.079 cm).

Figure 13:
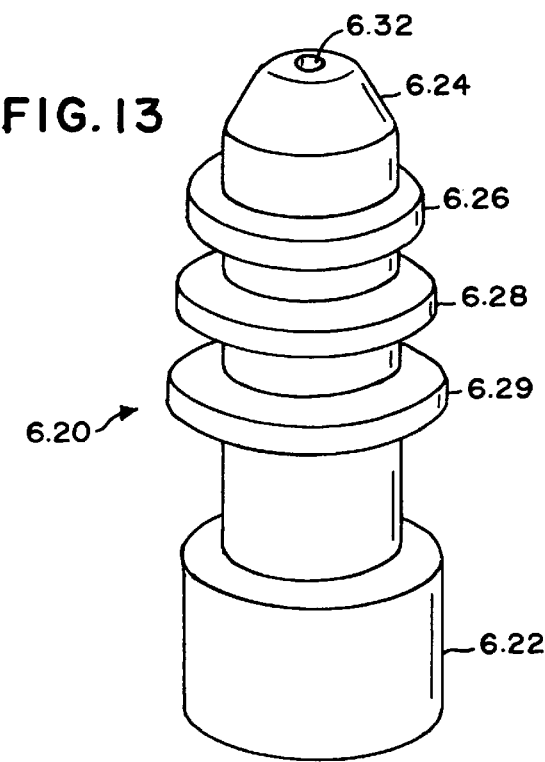
FIG. 13 is a side perspective view of a sixth embodiment of the present invention. The view from all sides is substantially the same.
Figure 14:
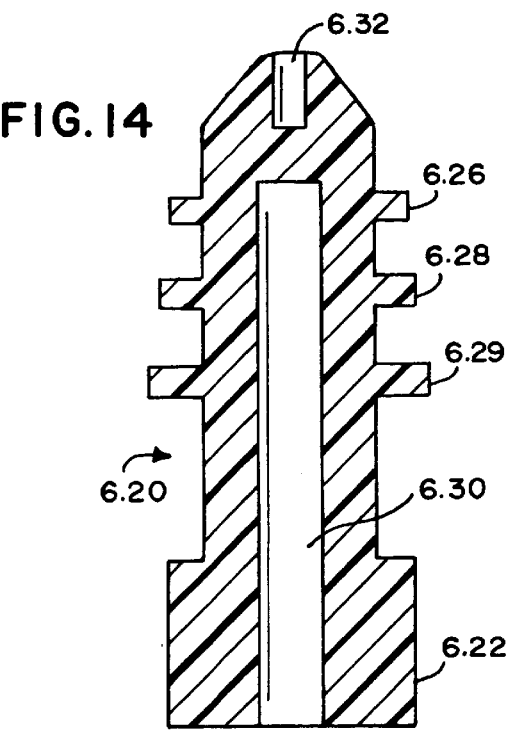
FIG. 14 is a longitudinal cross-sectional view of the sixth embodiment of the present invention. All longitudinal cross-sectional views along the axis of the sixth embodiment are substantially the same.

A sixth preferred embodiment is shown in FIGS. 13–14, with identifying reference designators marked similarly to the first through third embodiments, except with the prefix "6." It shall be understood that many aspects of all embodiments are substantially the same, and only the differences will be treated in detail.

The sixth embodiment 6.20 shown in FIGS. 13–14 is similar to the second embodiment 2.20 heretofore described, and the top view of the sixth embodiment is similar to the top view of the second embodiment shown in FIG. 5. The significant structural difference between the second and sixth embodiments is that the internal void 6.30 of the sixth embodiment is externally open at the base end rather than being a closed void as is internal void 2.30 of the second embodiment.

The sixth preferred embodiment of the present invention is seen to comprise a stand-alone earplug 6.20, preferably cylindrically symmetrical along an axis and being generally bullet-shaped, with a base 6.22 configured to rest in the concha of the ear of the user and a nose 6.24 configured to enter and block the auditory canal of the ear of the user. The base 6.22 of the earplug 6.20 nestles in the concha and is effectively held in place. The diameter of the earplug 6.20 ranges from about ³⁄₁₆ inch (0.476 cm) to about ⁹⁄₁₆ inch (1.43 cm), with the nominal diameter being smallest at the nose 6.24 of the earplug 6.20 and reaching its maximum at the base 6.22 of the earplug 6.20. The length of earplug 6.20 preferably ranges from about ¾ inch (1.91 cm) to about 1.5 inches (3.81 cm). The nose portion 6.24 of the earplug 6.20 may have one or more deformable highly flexible disks 6.26, 6.28, 6.29 for the purpose of creating multiple layers of sound blocking and enhancing comfort. The disks 6.26, 6.28, 6.29 are mounted laterally on the nose 6.24 of the earplug 6.20 so as to form flexible encircling flanges as shown. Individual disks 6.26 may vary in diameter to facilitate acoustically isolating different size ear canals. Open internal void 6.30, formed within earplug 6.20 via slush molding or injection molding, as heretofore described, may be of varying dimensions to allow compression of the earplug 6.20 before and during insertion into the wearer's ear. Earplug 6.20 also has a blind bore 6.32 formed as shown in the center of the nose portion 6.24 to further allow compression of the earplug before insertion into the ear of the user. The preferred embodiment of the stand-alone earplug 6.20 measures about ³⁄₁₆ inch (0.476 cm) in diameter at nose 6.24, ⁷⁄₁₆ inch (1.11 cm) in diameter at base 6.22, and 1.125 inches (2.86 cm) in length along the axis.

A common feature of all embodiments of the present invention and as shown in the drawings is that the plastisol is exposed circumferentially on an outer surface of the earpiece/earplug so that the exposed plastisol sealingly contacts the ear canal and concha of the wearer's ear when the earplug is received into the wearer's ear canal and concha.

Testing was conducted to evaluate formulations of a satisfactory non-foamed polyvinyl chloride plastisol composition, and the following examples are indicative of this testing and its results. The tests are non-limiting and, although representative of successful formulae, do not present any metes or bounds to the range of alternatives that would produce an appropriate plastisol for use in earplugs of the present invention. Various ranges of hardness are achievable by varying the formulation's percentage of polymer resin. However, the preferred embodiments as set forth in these examples produce a satisfactory result for both sound attenuation and for comfort. The range of ingredients and proportions thereof that may be varied broadly within the chemical families described herein to provide a broad base of plastisol ingredients from which specific embodiments may be produced. All of the tests performed on these four formulations were performed using earplugs shaped similar to those shown in FIG. 6, but without the internal void 3.30 shown in FIG. 7.

Each formulation test was conducted using a combination of laboratory and factory-type environments. Initial tests were conducted in a laboratory using wooden molds for the earpieces and manual mixing, injecting, and extracting of the earpieces. Subsequently, testing was performed in a factory setting to confirm the results in an industrial setting. Although factory and laboratory test results were substantially the same, the results of testing in a factory setting are presented here because they replicate the environment in which the present invention is contemplated to be used.

A first formulation is described in Table 1, below, and the text following.

TABLE 1

EXAMPLE 1

| Material | Parts by Weight | wt. % |
|---|---|---|
| Dioctyl Adipate plasticizer | 400 | 67.8 |
| Dioctyl Phthalate plasticizer | 70 | 11.9 |
| Vinyl chloride homopolymer | 100 | 16.9 |
| Epoxyized soy bean oil plasticizer/stabilizer | 10 | 1.7 |
| Calcium and zinc heat stabilizer | 10 | 1.7 |
| Pigment | As required | As required |

Dioctyl Adipate ("DOA") is a material approved by the U.S. Food and Drug Administration ("FDA") for human use, and humans can ingest up to two cups of DOA per day without harm. Although the earpieces of the present invention are not ingested, such an FDA-approved material is chosen because the earpiece contacts human skin when placed within the ear.

DOA and Dioctyl Phthalate ("DOP") are plasticizers of this formulation, and DOP is a lower-cost plasticizer than DOA. The vinyl chloride homopolymer was chosen for low cost because copolymers are somewhat more expensive. The epoxidized soybean oil acts as a plasticizer/stabilizer, and the calcium and zinc acts as a heat stabilizer.

An acceptable DOA for use in this formulation, and which was used in these tests, is that sold under the trademark Eastman DOA, an adipate plasticizer produced by Eastman Chemical located in Kingsport, Tenn. An acceptable DOP for use in this formulation, and which was used in these tests, is that sold under the trademark Eastman DOP, a phthalate plasticizer also produced by Eastman Chemical. An acceptable vinyl chloride homopolymer for use in this formulation, and which was used in these tests, is that sold under the trademark OxyChem 74GP, a general purpose homopolymer of vinyl chloride produced by Occidental Chemical located in Dallas, Tex. An acceptable calcium and zinc heat stabilizer for use in this formulation, and which was used in these tests, is that sold under the trademark 760X and produced by Ferro Corporation located in Bedford, Ohio.

If desired, chlorinated paraffin and/or antimony trioxide could be added as a fire suppressant/fire retardant. As the chlorinated paraffin is heated during processing, the chlorine is released and acts as a fire retardant. Antimony trioxide, if added, also acts as a fire retardant.

This plastisol formulation was stored for three weeks to check gelation properties and to ensure good shelf life of the raw and unprocessed formulation, which proved satisfactory. The plastisol liquid, at room temperature, was then pumped into a holding tank and heated to a temperature of 350° Fahrenheit (177° Celsius) to complete th e fusion process. Fused plastisol was injected into a mold, cooled to room temperature, then removed from the mold. The resultant earplugs were of a homogeneous and supple plastic that was allowed to cure at room temperature for three days. The cured earplugs were then measured for hardness using an ASTM D2240-compliant 00 Durometer and yielded a hardness reading of 47. Testing the earplugs in a sound booth conforming to ANSI S12.6-1997 yielded a noise reduction rating ("NRR") range from 24 dB to 36 dB.

A second formulation is described in Table 2, below, and the text following.

TABLE 2

EXAMPLE 2

| Material | Parts by Weight | wt. % |
|---|---|---|
| Dioctyl Adipate plasticizer | 470 | 79.7 |
| Vinyl chloride homopolymer | 100 | 16.9 |
| Epoxyized soy bean oil plasticizer/stabilizer | 10 | 1.7 |
| Calcium and zinc heat stabilizer | 10 | 1.7 |
| Pigment | As required | As required |

Again, if desired, chlorinated paraffin and/or antimony trioxide could be added as a fire suppressant/fire retardant.

The second formulation used somewhat more-expensive ingredients but was otherwise substantially similar to the first formulation, and the substantial difference between the first and second formulations is that, in the second formulation, DOA alone was used as the plasticizer in the same amount as the total plasticizer (DOA plus DOP) in the first formulation. Recent research has shown the possibility that DOP may be a carcinogen, so the second formulation, while somewhat more expensive than the first formulation, was created to allow testing of the invention's formulation with carcinogen-free ingredients.

Satisfactory gelation properties were demonstrated after storing this formulation for three weeks. The formulation was pumped into a holding tank where it was heated to a temperature of 350° Fahrenheit (177° Celsius). The fused plastisol liquid was then injected into a mold, cooled to room temperature, then removed from the mold. The resultant earplugs were of equivalent suppleness. After a three-day curing period at room temperature, the earplugs were measured for hardness using an ASTM D2240 compliant 00 Durometer and yielded a hardness reading of 45. Testing the earplugs in a sound booth conforming to ANSI S12.6-1997 yielded a noise reduction rating ("NRR") range from 20 dB to 30 dB.

To determine the optimum hardness, two additional formulations were prepared using the ingredients listed for the first two formulation experiments described above. The third formulation used the ingredients listed in the first example (Table 1), but added an additional 30 parts of vinyl chloride homopolymer, and the fourth formulation used the ingredients listed in the second example (Table 2), but added 60 parts of vinyl chloride homopolymer, thereby varying the amount of resin so as to alter the hardness of the resulting earpiece. The modified formulations were found to exhibit a hardness of 58 and 61, respectively, using an ASTM D2240-compliant 00 Durometer. Testing the earplugs in a sound booth conforming to ANSI S12.6-1997 yielded a noise reduction rating ("NRR") range from 16 dB to 26 dB and from 16 dB to 24 dB, respectively.

Figure 10:
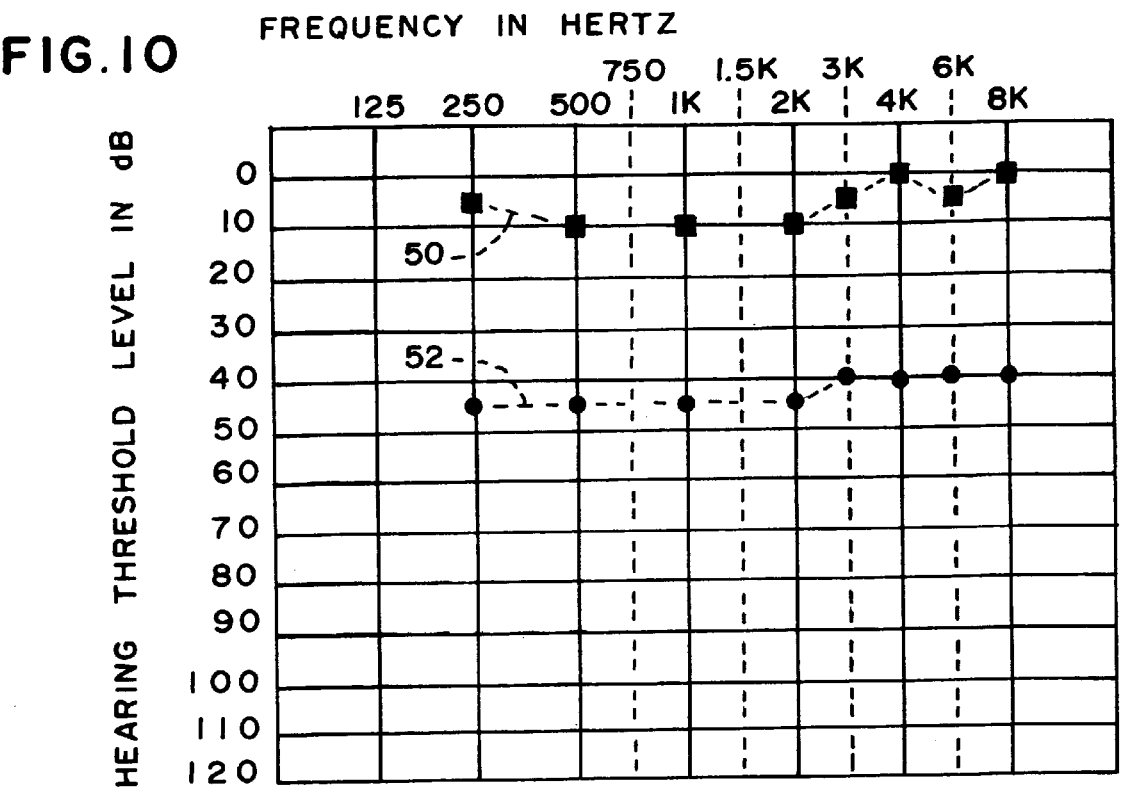
FIG. 10 is a graph showing the results of audiologic evaluation tests of earplugs made from a first formulation of the present invention.
Figure 11:
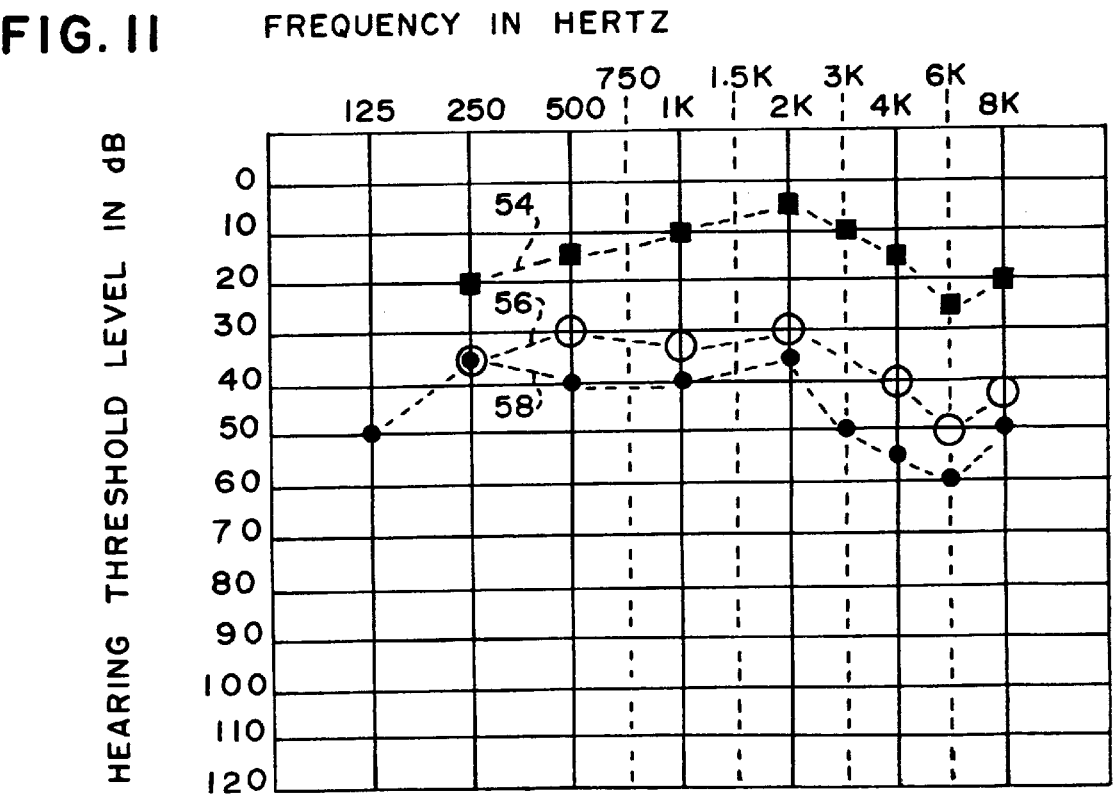
FIG. 11 is a graph showing the results of audiologic evaluation tests of earplugs made from second and third formulations of the present invention.
Figure 12:
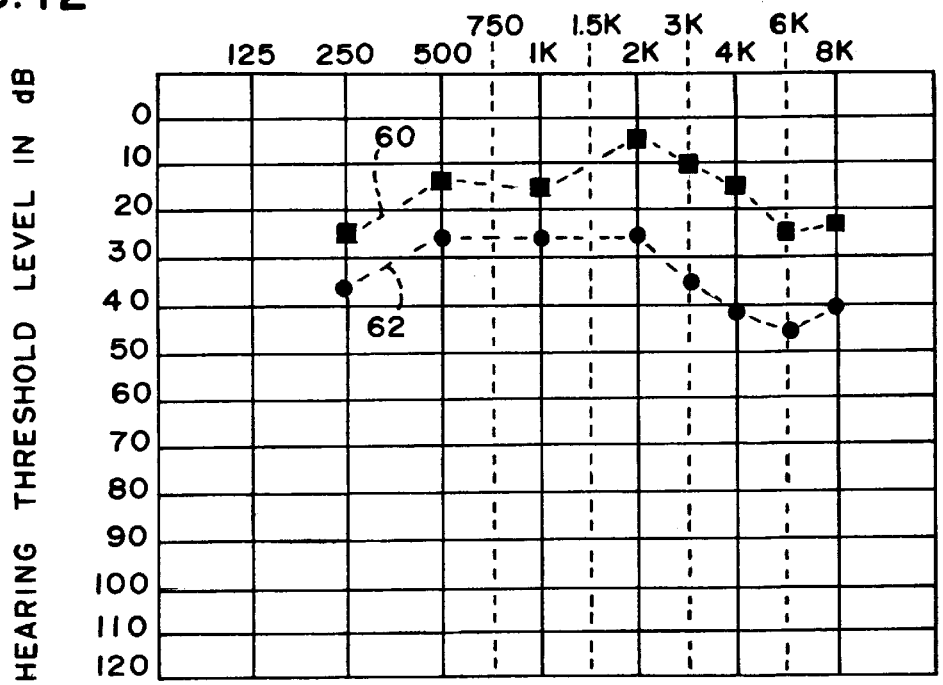
FIG. 12 is a graph showing the results of an audiologic evaluation tests of earplugs made from a fourth formulation of the present invention.

FIGS. 10–12 show graphs depicting results of audiologic tests that were conducted on these various formulations of the present invention. The tests shown in FIG. 10 were performed on a first test subject, while the tests shown in FIGS. 11–12 were performed on a second test subject. All tests were performed at a room temperature of about 70° Fahrenheit (21° Celsius).

FIG. 10 shows the results of an audiologic evaluation of earplugs made from the first formulation described above. The line 50 marked with a square box shows a baseline frequency response in decibels when the subject was not wearing the earplugs of the present invention, i.e., with unoccluded/open ears. The line 52 marked with a solid black circle shows the frequency response in decibels of sound occluded at the same frequencies when the subject was wearing the earplugs of the first formulation of the present invention. The test results of FIG. 10 for the first formulation show an average of about 36 dB of sound reduction from the baseline frequency response when averaged across the tested audio frequencies.

FIG. 11 shows the results of an audiologic evaluation of earplugs made from the second and third formulations described above. The line 54 marked with a square box shows a baseline frequency response in decibels when the subject was not wearing the earplugs of the present invention, i.e., with open ears, and the test results show an average of about 17 dB of unoccluded sound loss of this test subject's hearing when averaged across the tested audio frequencies. The line 56 marked with an open circle shows the frequency response in decibels of sound occluded at the same frequencies when the subject was wearing the earplugs of the second formulation of the present invention. The test results 56 of FIG. 11 for the second formulation show an average of 38 dB of sound reduction as compared with the baseline frequency response 54 when averaged across the tested audio frequencies. The line 58 marked with a solid black circle shows the frequency response in decibels of sound occluded at the same frequencies when the subject was wearing the earplugs of the third formulation of the present invention. The test results 58 of FIG. 11 for the third formulation show an average of about 40 dB of sound reduction as compared with the baseline frequency response 54 when averaged across the tested audio frequencies.

FIG. 12 shows the results of an audiologic evaluation of earplugs made from the fourth formulation described above. The line 60 marked with a square box shows a baseline frequency response in decibels when the subject was not wearing the earplugs of the present invention, i.e., with unoccluded/open ears, and the test results show an average of 16.8 dB of sound loss when averaged across the tested audio frequencies, which is consistent with the unoccluded baseline 54 shown in FIG. 11 for this same subject. The line 62 marked with a solid black circle shows the frequency response in decibels of sound occluded at the same frequencies when the subject was wearing the earplugs of the fourth formulation of the present invention. The test results 62 for the fourth formulation show an average of 33.75 dB of sound attenuation from a 0 dB level when averaged across the tested audio frequencies. A comparison of test results 62 with the baseline test results 60 thus shows an average improvement of about 17 dB of sound reduction when wearing the earplugs of the fourth formulation as compared to not wearing the earplugs. As expected, the relatively harder fourth formulation of the earplugs of the present invention do not provide as great a sound attenuation as does the somewhat softer second and third formulations.

Although the present invention has been described and illustrated with respect to a preferred embodiment and a preferred use therefor, it is not to be so limited since modifications and changes can be made therein which are within the full intended scope of the invention.

We claim:

1. An earplug comprised of non-foamed polyvinyl chloride plastisol having a formulation comprising at least 65 wt. % of a plasticizer and adapted for receipt into a human being's concha.

2. The earplug as recited in claim 1, wherein said earplug has an internal void formed therewithin.

3. The earplug as recited in claim 1, wherein said earplug has a closed internal void formed therewithin.

4. The earplug as recited in claim 1, wherein said earplug has a 00 Durometer hardness value ranging between 10 and 90.

5. The earplug as recited in claim 1, wherein said earplug has a 00 Durometer hardness value ranging between 40 and 60.

6. The earplug as recited in claim 1, wherein said earplug has a 00 Durometer hardness value ranging between 40 and 60, and has a closed internal void formed therewithin.

7. An earplug comprised of non-foamed polyvinyl chloride plastisol and adapted for receipt into a human being's concha; said plastisol including no blowing agent, and said plastisol comprising:
   (a) 65 to 90 wt. % of a plasticizer, said plasticizer being selected from the group consisting of a dibasic acid, a glycol, a monobasic fatty acid, alcohol, and hydroxyl; and
   (b) 10 to 30 wt. % of a resin, said resin being selected from the group consisting of soybean oil, linseed oil, triglycerides, alkyl esters of oleic acid, alkyl esters of tall oil fatty acids, epoxides of tall oil fatty acid bis-esters of ethylene, propylene glycol, polyvinyl homopolymers, and polyvinyl copolymers.

8. The earplug as recited in claim 1, in which said plastisol is exposed on an outer surface of said earplug so that said exposed plastisol sealingly contacts an ear canal of the human being when said earplug is received into the human being's concha.

9. The earplug as recited in claim 8, in which said earplug is generally cylindrically symmetrical and has a diameter between about 0.476 cm to 1.43 cm, inclusive.

10. An earplug comprised of non-foamed polyvinyl chloride plastisol having a formulation comprising at least 65 wt. % of a plasticizer and adapted for substantially blocking an ear canal of a human being.

11. The earplug as recited in claim 10, wherein said earplug has an internal void formed therewithin.

12. The earplug as recited in claim 10, wherein said earplug has a closed internal void formed therewithin.

13. The earplug as recited in claim 10, wherein said earplug has a 00 Durometer hardness value ranging between 10 and 90.

14. The earplug as recited in claim 10, wherein said earplug has a 00 Durometer hardness value ranging between 40 and 60.

15. The earplug as recited in claim 10, wherein said earplug has a 00 Durometer hardness value ranging between 40 and 60, and has a closed internal void formed therewithin.

16. An earplug comprised of non-foamed polyvinyl chloride plastisol and adapted for substantially blocking an ear canal of a human being; said plastisol including no blowing agent, and said plastisol comprising:
   (a) 65 to 90 wt. % of a plasticizer, said plasticizer being selected from the group consisting of a dibasic acid, a glycol, a monobasic fatty acid, alcohol, and hydroxyl; and
   (b) 10 to 30 wt. % of a resin, said resin being selected from the group consisting of soybean oil, linseed oil, triglycerides, alkyl esters of oleic acid, alkyl esters of tall oil fatty acids, epoxides of tall oil fatty acid bis-esters of ethylene, propylene glycol, polyvinyl homopolymers, and polyvinyl copolymers.

17. The earplug as recited in claim 10, in which said plastisol is exposed on an outer surface of said earplug so that said exposed plastisol sealingly contacts the ear canal of the human being.

18. The earplug as recited in claim 17, in which said earplug is generally cylindrically symmetrical and has a diameter between about 0.476 cm to 1.43 cm, inclusive.

19. An earpiece comprised of non-foamed polyvinyl chloride plastisol having a formulation comprising at least 65 wt. % of a plasticizer and adapted for covering an electrical to audio sound reproduction device and also for being received into a human being's concha.

20. The earpiece as recited in claim 19, in which said plastisol is exposed on an outer surface of said earpiece so that said exposed plastisol sealingly contacts the concha of the human being when said earpiece is received into the human being's concha.

* * * * *